United States Patent
Shi et al.

(10) Patent No.: US 11,427,528 B2
(45) Date of Patent: Aug. 30, 2022

(54) FENOFIBRATE CRYSTALLINE FORM AND MANUFACTURING METHOD THEREOF

(71) Applicants: Zhejiang University of Technology, Zhejiang (CN); Hangzhou SoliPharma Co., Ltd., Zhejiang (CN)

(72) Inventors: Xiangjun Shi, Zhejiang (CN); Yinghua Shao, Zhejiang (CN); Xiaohong Sheng, Zhejiang (CN); Xiaoxia Sheng, Zhejiang (CN)

(73) Assignee: Hangzhou Solipharma Co., Ltd., Zhejiang (CN)

( * ) Notice: Subject to any disclaimer, the term of this patent is extended or adjusted under 35 U.S.C. 154(b) by 885 days.

(21) Appl. No.: 16/321,637

(22) PCT Filed: Jul. 29, 2016

(86) PCT No.: PCT/CN2016/092351
§ 371 (c)(1),
(2) Date: Jan. 29, 2019

(87) PCT Pub. No.: WO2018/018618
PCT Pub. Date: Feb. 1, 2018

(65) Prior Publication Data
US 2019/0270694 A1    Sep. 5, 2019

(51) Int. Cl.
*C07C 69/738* (2006.01)
*C07C 67/52* (2006.01)
*C07C 69/712* (2006.01)

(52) U.S. Cl.
CPC ............ *C07C 69/738* (2013.01); *C07C 67/52* (2013.01); *C07C 69/712* (2013.01); *C07B 2200/13* (2013.01)

(58) Field of Classification Search
CPC ............................. C07C 67/52; C07C 69/738
USPC ......................................................... 560/53
See application file for complete search history.

(56) References Cited

U.S. PATENT DOCUMENTS

| | | |
|---|---|---|
| 4,739,101 A | 4/1988 | Bourgogne et al. |
| 8,445,715 B2 | 5/2013 | Synkem |

FOREIGN PATENT DOCUMENTS

| | | |
|---|---|---|
| CN | 1993107 A | 7/2007 |
| CN | 104311422 A | 1/2015 |
| CN | 104478717 A | 4/2015 |
| EP | 2170801 B1 | 3/2014 |
| WO | WO-2014/187229 A1 | 11/2014 |

OTHER PUBLICATIONS

Di Martino, P., et al., "Evidence of a metastable form of fenofibrate," Pharmazie 55(8): 625-6, Govi-Verlag Pharmazeutischer Verlag GmbH, Germany (2000).
Sheu, M-T., et al., "Characterization and dissolution of fenofibrate dispersion systems," International Journal of Pharmaceutics 103(2):137-46, Elsevier, Netherlands (1994).
Yazdanpanah, N. et al., "Novel Technique for Filtration Avoidance in Continuous Crystallization," Crystal Growth & Design 16(1): 285-96, ACS Publications, United States (2016).
Tipduangta; P., et al., "A New Low Melting-Point Polymorph of Fenofibrate Prepared via Talc Induced Heterogeneous Nucleation," Crystal Growth & Design 15(10):5011-20, ACS Publications, United States (2015).
International Search Report and Written Opinion in International Application No. PCT/CN2016/092351, State Intellectual Property Office of the P.R. China, dated Apr. 28, 2017, 9 pages.

*Primary Examiner* — Ana Z Muresan
(74) *Attorney, Agent, or Firm* — Sterne, Kessler, Goldstein & Fox P.L.L.C.

(57) ABSTRACT

The present invention relates to Form IV of fenofibrate and its preparation methods thereof. Its X-ray powder diffraction pattern expressed as 2θ angle has characteristic peaks at 14.15±0.2°, 15.94±0.2°, 16.49±0.2°, 17.45±0.2°, 20.21±0.2°, and 22.87±0.2°. The present invention also provides preparation methods of Form IV. The preparation methods are simple, easy to operate, short, and have good repeatability. The methods are also non-toxic and non-polluting by using water as a medium and using a pharmaceutically accepted excipient, such as polyvinylpyrrolidone or polyvinyl alcohol as an inducer. The results of stability experiments (light exposure, high humidity and grinding) and solubility tests show that Form IV is stable and has a higher solubility than the prior art crystal form.

14 Claims, 2 Drawing Sheets

FENOFIBRATE CRYSTALLINE FORM AND MANUFACTURING METHOD THEREOF

FIELD OF THE INVENTION

The present invention relates to the technical filed of crystallization in pharmaceutical chemistry. Specifically, the present invention relates to a crystalline form IV of fenofibrate, and its preparation.

BACKGROUND

Fenofibrate is a drug of the fibrate class. It is mainly used to reduce cholesterol levels in patients at risk of cardiovascular diseases. Fenofibrate was first launched in 1975 and has been widely used around the world.

The chemical name of fenofibrate is 2-methyl-2-(4-(4-chlorobenzamide) phenoxy) isopropyl propionate with the following chemical structural shown in Formula I:

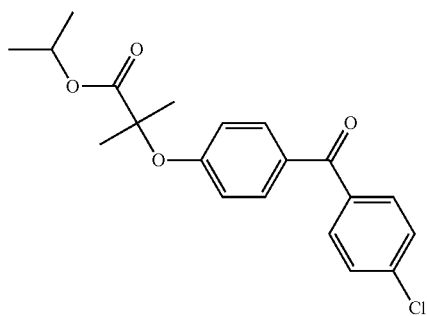

(I)

A chemical compound may exist in a variety of crystalline forms, this phenomenon is called polymorphism. Different crystalline forms have different packing arrangements and/or molecular conformation in crystal lattice. Different crystalline forms have different physical and chemical properties, such as X-ray powder diffraction (XRPD) patterns and IR spectra, stability and solubility. These different properties may have a direct impact on drug dissolution, bioavailability, processability and manufacturability. Patent CN1993107A reported the X-ray powder diffraction patterns of crystalline form I (hereinafter referred to as Form I) and crystalline form II (hereinafter referred to as Form II) of fenofibrate.

A journal article (Chem. Pharm. Bull., 2000, 55: 625-626) disclosed Form II of fenofibrate with a differential scanning calorimetry (DSC) melting point at about 74° C. The article stated that Form II was unstable and transformed to Form I after two days at room temperature, and transformed to Form I after mechanical grinding.

A Journal article (Cryst. Growth Des, 2015, 10:5501-5520) reported a crystalline form III (hereinafter referred to as Form III) of fenofibrate and its X-ray powder diffraction pattern. It described that Form I is the most stable form, while Form II and Form III are metastable forms. It also described that Form III transformed to Form II and Form I at room temperature in one day.

According to above journal articles, Form II and Form III are unstable, and only Form I is considered to have pharmaceutical value. Fenofibrate is a compound that is almost insoluble in water. Form I of fenofibrate has poor solubility, and thus poor bioavailability. Therefore, there is a need to discover new crystalline forms of fenofibrate with both higher solubility and good stability.

SUMMARY OF THE INVENTION

The objective of the present invention is to provide a crystalline form IV (hereinafter referred to as Form IV) of fenofibrate with improved solubility and stability.

FIG. 2 is the X-ray powder diffraction pattern of Form IV of fenofibrate of the present invention. Form IV is characterized by X-ray diffraction pattern having specific peaks at 7.98±0.2°, 9.82±0.2°, 12.96±0.2°, 14.15±0.2°, 15.94±0.2°, 16.49±0.2°, 17.45±0.2°, 17.99±0.2°, 18.79±0.2°, 20.21±0.2°, 22.87±0.2°, and 26.17±0.2°.

FIG. 4 is the Fourier transform infrared (FTIR) spectrum of Form IV of fenofibrate of the present invention. Form IV has characteristic peaks at wave numbers of 2985±2 $cm^{-1}$, 2936±2 $cm^{-1}$, 1737±2 $cm^{-1}$, 1650 $cm^{-1}$, 1596±2 $cm^{-1}$, 1499±2 $cm^{-1}$, 1468±2 $cm^{-1}$, 1389±2 $cm^{-1}$, 1314±2 $cm^{-1}$, 1258±2 $cm^{-1}$, 1149±2 $cm^{-1}$, and 1093±2 $cm^{-1}$.

FIG. 3 is the differential scanning calorimetry (DSC) thermogram of Form IV of fenofibrate of the present invention.

Another objective of the present invention is to provide a method for preparing Form IV of fenofibrate. The method comprises the following steps: mixing fenofibrate Form I and a polymer, adding a solvent, stirring to promote uniform mixing, heating until fenofibrate melts, cooling to crystallize, filtering, washing the filtration cake, and drying to obtain Form IV.

Preferably, the polymer is selected from the group consisting of polyvinylpyrrolidone and polyethylene-glycol.

Preferably, the amount of the polymer is 1% to 20% of the weight of fenofibrate, more preferably 5% to 10%.

Preferably, the solvent is selected from a protic solvent, more preferably water.

Preferably, the weight-to-volume ratio of fenofibrate and the solvent ranges from 100 mg:1 mL to 1000 mg:1 mL, more preferably from 100 mg:1 mL to 200 mg:1 mL.

Preferably, the solvent is heated to a temperature ranging from 80° C. to 100° C., more preferably from 85° C. to 92° C.

Preferably, the solvent is cooled to a temperature ranging from −20° C. to 30° C., more preferably room temperature.

Non-restrictively, the present invention provides other preparation methods of Form IV of fenofibrate, such as melting Form I of fenofibrate in a solvent to form a solution or forming a suspension of Form I of fenofibrate and then cooling or volatilizing to crystallize to obtain Form IV. Preferably, a small amount of seed crystals of Form IV of fenofibrate can be added before crystallization, and the seed crystals can be prepared according to a method of the present invention.

The Form IV of fenofibrate of the present invention and its preparation methods thereof have the following beneficial effects compared with the known crystalline forms of fenofibrate:

Form IV has higher solubility in water than the known Form I; since water solubility is an indication of bioavailability, Form IV is expected to have a better bioavailability than the known Form I. In particular, fenofibrate molecules have hydrophobic groups and poor solubility. Form IV of fenofibrate of the present invention can better address the problems of limited medicinal value of fenofibrate caused by its low solubility and low bioavailability.

The preparation methods of Form IV are simple, short, easy to operate, and have good repeatability. The preparation methods are non-toxic and environmentally friendly by using water as the medium and using a pharmaceutically acceptable excipient such as polyvinylpyrrolidone or polyethylene glycol as an inducer.

Form IV remains stable at room temperature for 3 months. Form IV does not change its crystalline form after storing for 10 days at 25° C. under 4500±500 lx light exposure and 90±5% relative humidity chamber, respectively. Form IV does not change its crystalline form after grinding for 10 minutes. The results indicate that Form IV has good stability and is suitable for pharmaceutical production and drug storage.

According to the above preparation methods of the present invention:

The "room temperature" is a temperature between 10° C. and 30° C.

"Stirring" may be carried out by a conventional stirring method in the art, such as magnetic stirring, mechanical stirring, and the stirring speed is 50-1800 r/min, preferably 300-900 r/min.

The protic solvent refers to a solvent containing a hydroxyl group or an amino group, such as water, an alcohol, or an amine.

The polymers are pharmaceutically acceptable natural or synthetic polymers with good biocompatibility, and many of them are common pharmaceutical excipients. Depending on the number of monomers in the polymer, the molecular weight of the polymer can range from 1000 to 3,000,000. The polymer includes, but not limited to, polyethylene, polypropylene, polyvinyl chloride, polyvinylidene chloride, polyvinyl alcohol, polyoxyethylene, polyethylene glycol, polylactic acid, cellulose such as methyl cellulose, ethyl cellulose, hydroxypropyl cellulose, hypromellose, hydroxybutyl methyl cellulose, cellulose acetate, cellulose propionate, cellulose acetate butyrate, vinegar cellulose, hydroxymethylcellulose, cellulose triacetate, carboxymethylcellulose sodium, povidone, polyacrylic acid, polyallylamine hydrochloride, polymethyl methacrylate, poloxamer, crospovidone, polyolefin-based diol, polycaprolactone, polylactic acid-glycolic acid copolymer, carbomer, polycarbophil calcium, and the like.

The Form IV of fenofibrate of the present invention is substantially pure and substantially free of any other crystalline or amorphous forms. When referring to a new crystalline form, the term "substantially pure" means that the new crystalline form comprises at least 80% by weight of the compound present, more preferably at least 90% by weight, especially at least 95% by weight, in particular at least 99% by weight. The "crystalline form" in the present invention is confirmed by the X-ray powder diffraction pattern. It is known to those skilled in the field that experimental errors of X-ray diffraction depend on instrument conditions, sample preparation and sample purity. The 2θ angle of the peaks in the X-ray powder diffraction pattern usually varies slightly due to the difference in the instrument and sample. The differences in peak position may vary by 1°, 0.8°, 0.5°, 0.3°, or 0.1° 2θ, depending on different instruments and samples, and usually ±0.2° in differences are allowed. The relative intensities of peaks may change with the change of samples, sample preparation and other experimental conditions; therefore, the order of peak intensities should not be regarded as the only or the determining factor. Due to the effect of experimental factors including sample height, peak position may shift; generally, a small amount of peak shifting is acceptable experimental error. Hence, it is well understood for those skilled in the field that any fenofibrate material having the same or similar X-ray powder diffraction pattern as that of the crystalline form in the present invention should be within the scope of the present invention. "Pure crystalline form" refers to a pure crystalline form confirmed by X-ray powder diffraction.

In the present invention, the fenofibrate starting material is Form I, which is commercially available and has a white to off-white appearance.

The various reagents used in Examples are commercially available unless otherwise indicated.

In Examples, a procedure is operated at room temperature unless otherwise indicated.

EXAMPLES

The following examples are provided to illustrate some aspects of the present invention. The examples, however, are not intended to limit the scope of any embodiment of the present invention.

Instrument and Method for Data Collection:

The instrument used for collecting X-ray powder diffraction (XRPD) patterns is Bruker D8 Advance diffractometer. The samples are tested at room temperature under the following conditions: 2θ scan range, 3-40°; step size, 0.02°/step; speed, 0.2 s/step.

Differential scanning calorimetry data are collected on TA Instruments Q200 MDSC. The procedure is as follows: Usually take 1-10 mg sample and heat it to 100° C. under the protection of 40 ml/min dry nitrogen at a heating rate of 10° C./min.

The infrared spectra are collected using Burker Tensor 27 FT-IR. Test method: Making a potassium bromide blank pellet and sample pellets, and then record infrared spectra.

The solubility data are collected using the TU-1901 ultraviolet spectrophotometer at a wavelength of 289 nm.

Example 1

Mixed fenofibrate Form I (100 mg) and polyvinylpyrrolidone PVP K30 (5 mg), added the mixture to water (1.0 mL), heated to 92° C. until fenofibrate was melted in water to form an emulsion, stirred, cooled to room temperature until solids were precipitated, filtered, washed the wet cake using a small amount of water and dried the wet cake under vacuum at room temperature for 4 hours to obtain fenofibrate Form IV (82 mg, 82% yield).

Figure 1:
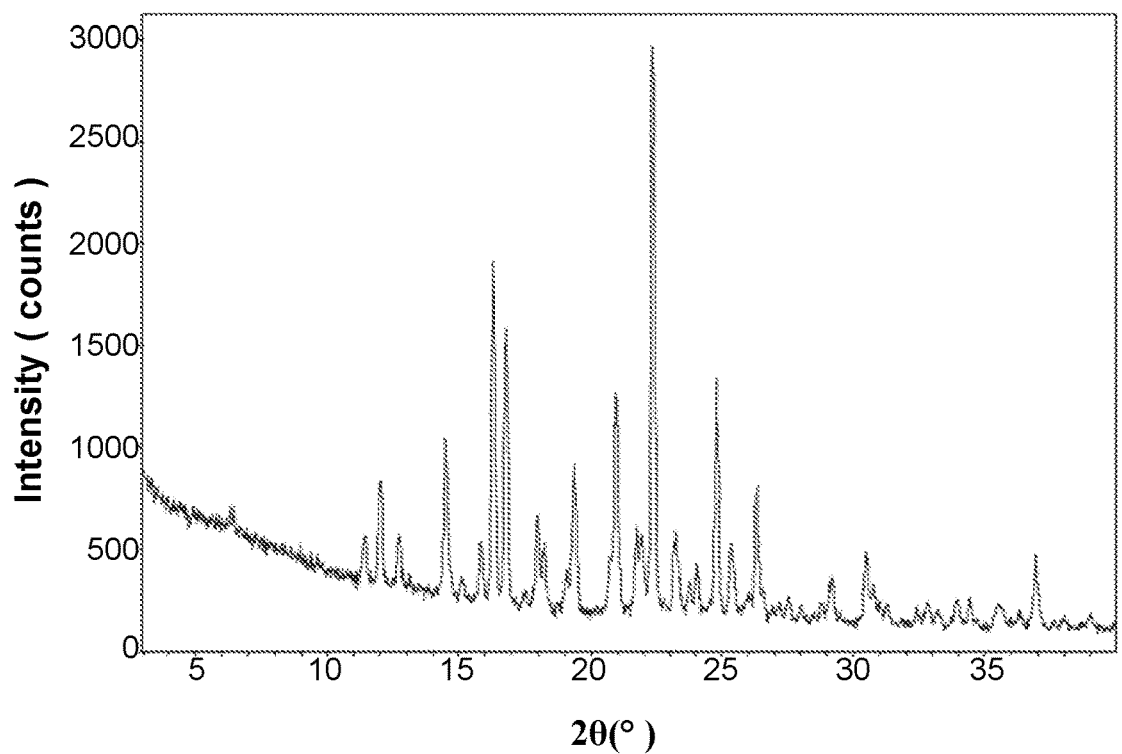
FIG. 1 is the XRPD pattern of fenofibrate Form I.
Figure 2:
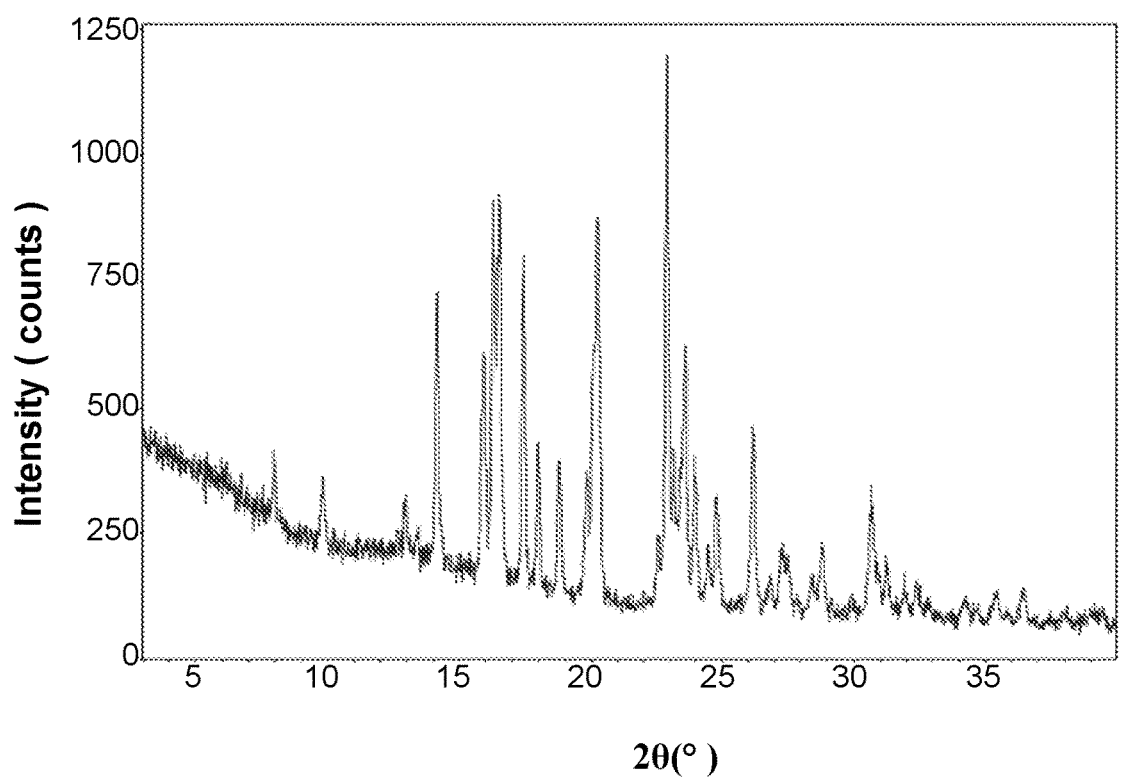
FIG. 2 is the XRPD pattern of fenofibrate Form IV according to Example 1 of the present invention.
Figure 3:
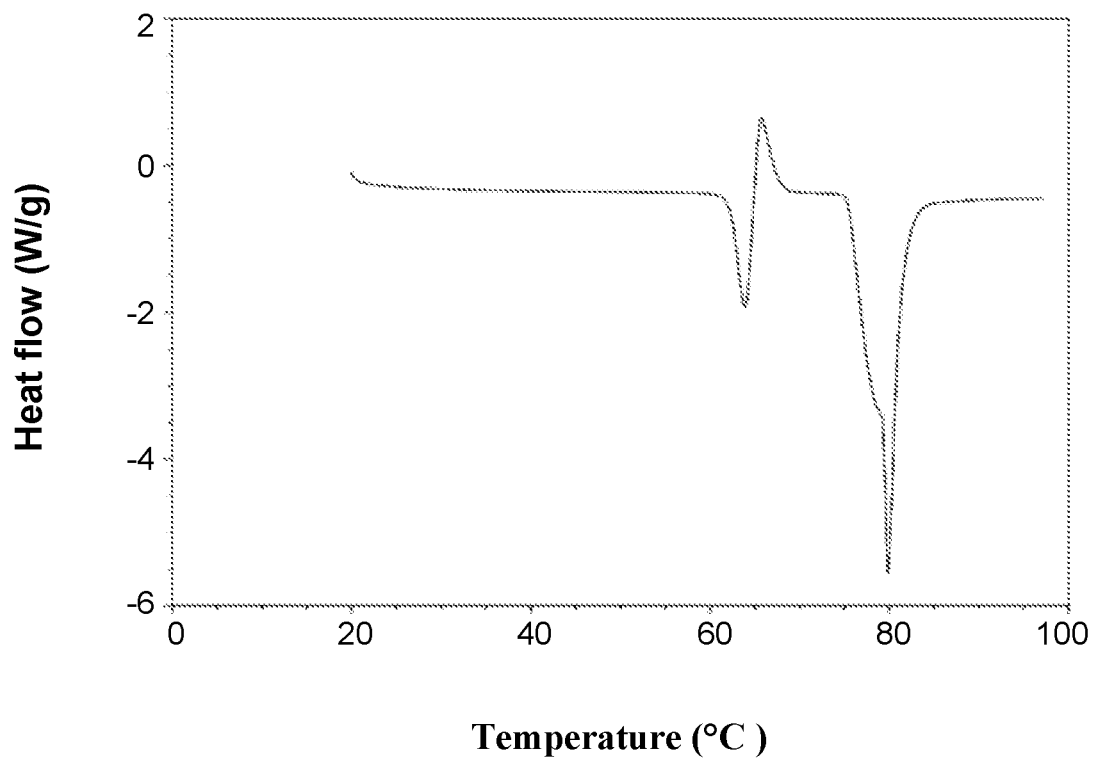
FIG. 3 is the DSC pattern of fenofibrate Form IV according to Example 1 of the present invention.
Figure 4:
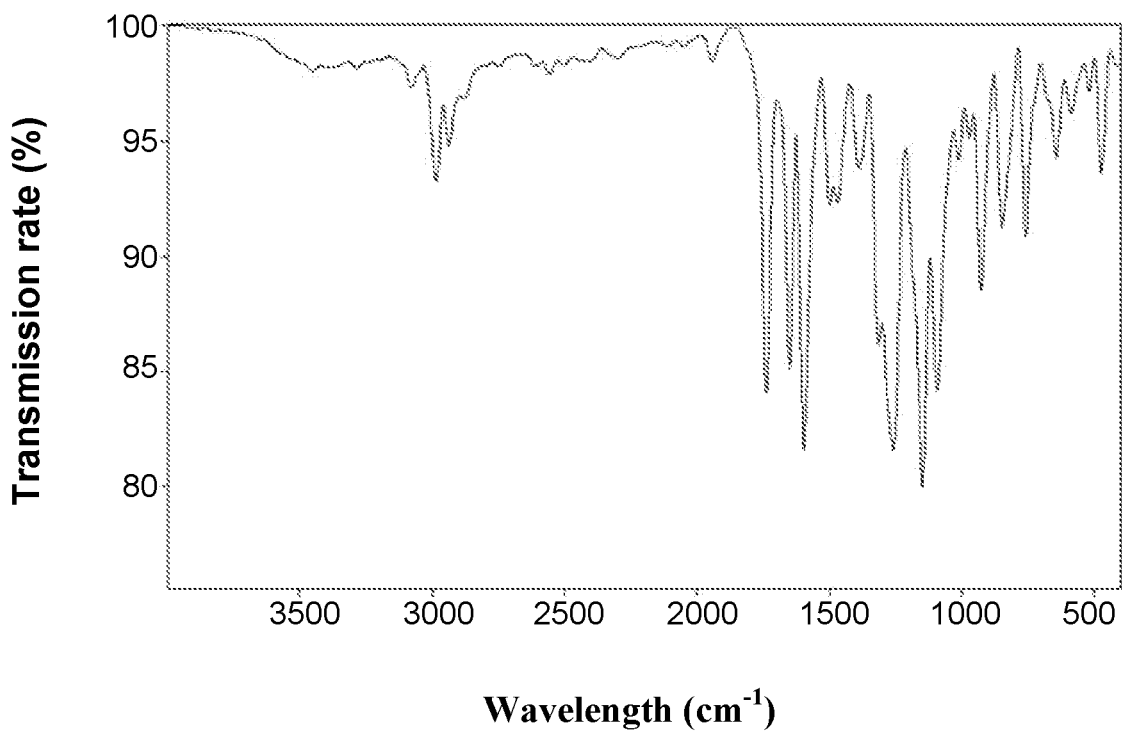
FIG. 4 is the IR pattern of fenofibrate Form IV according to Example 1 of the present invention.

FIG. 2 is the XRPD pattern of Form IV of fenofibrate. FIG. 3 is the DSC pattern of Form IV of fenofibrate. FIG. 4 is the IR spectrum of Form IV of fenofibrate.

Example 2

Mixed fenofibrate Form I (100 mg) and PVP K40 (2.5 mg), added the mixture to water (1.0 mL), heated to 85° C. until fenofibrate was melted in water to form an emulsion, stirred, cooled to room temperature until solids were precipitated, filtered, washed the wet cake using a small amount of water and dried the wet cake under vacuum at room temperature for 4 hours to obtain fenofibrate Form IV (80 mg, 80% yield).

Example 3

Mixed fenofibrate Form I (100 mg) and PVP K40 (10 mg), added the mixture to water (1.0 mL), heated to 90° C. until fenofibrate was melted in water to form an emulsion, stirred, cooled to room temperature until solids were precipitated, filtered, washed the wet cake using a small amount of water and dried the wet cake under vacuum at room temperature for 4 hours to obtain of fenofibrate Form IV (86 mg, 86% yield).

Example 4

Mixed fenofibrate Form I (100 mg) and polyethylene glycol 4000 (5 mg), added the mixture to water (1.0 mL), heated to 90° C. until fenofibrate was melted in water to form an emulsion, stirred, cooled to room temperature until solids were precipitated, filtered, washed the wet cake using a small amount of water and dried the wet cake under vacuum at room temperature for 4 hours to obtain fenofibrate Form IV (88 mg, 88% yield).

Example 5

Mixed fenofibrate Form I (100 mg) and polyethylene glycol 6000 (1 mg), added the mixture to water (1.0 mL), heated to 100° C. until fenofibrate was melted in water to form an emulsion, stirred, cooled to room temperature until solids were precipitated, filtered, washed the wet cake using a small amount of water and dried the wet cake under vacuum at room temperature for 4 hours to obtain fenofibrate Form IV (75 mg, 75% yield).

Example 6

Mixed fenofibrate Form I (100 mg) and polyethylene glycol 10000 (20 mg), added the mixture to water (1.0 mL), heated to 90° C. until fenofibrate was melted in water to form an emulsion, stirred, cooled to room temperature until solids were precipitated, filtered, washed the wet cake using a small amount of water and dried the wet cake under vacuum at room temperature for 4 hours to obtain fenofibrate Form IV (81 mg, 81% yield).

Example 7

Mixed fenofibrate Form I (100 mg) and PVP K30 (2 mg), added the mixture to water (0.5 mL), heated to 90° C. until fenofibrate was melted in water to form an emulsion, stirred, cooled to room temperature until solids were precipitated, filtered, washed the wet cake using a small amount of water and dried the wet cake under vacuum at room temperature for 4 hours to obtain fenofibrate Form IV (81 mg, 81%).

Example 8

Mixed fenofibrate Form I (200 mg) and polyethylene glycol 2000 (2 mg), added the mixture to n-butanol (0.2 mL), heated to 80° C. until fenofibrate was melted in n-butanol to form an emulsion, stirred, cooled to 0° C. until solids were precipitated, filtered, washed the wet cake using a small amount of water and dried the wet cake under vacuum at room temperature for 4 hours to obtain fenofibrate Form IV (50 mg, 25% yield).

Example 9

Mixed fenofibrate Form I (200 mg) and polyethylene glycol 4000 (20 mg), added the mixture to monoethanolamine (0.2 mL), heated to 80° C. until fenofibrate was melted in monoethanolamine to form an emulsion, stirred, cooled to −20° C. until solids were precipitated, filtered, washed the wet cake using a small amount of water and dried the wet cake under vacuum at room temperature for 4 hours to obtain of fenofibrate Form IV (74 mg, 37% yield).

Example 10

Placed fenofibrate Form I (100 mg) in water (1.0 mL), heated to 92° C. until fenofibrate was melted in water to form an emulsion, stirred, cooled to 80° C. and added seed crystal of fenofibrate Form IV (1 mg), cooled to room temperature until solids were precipitated, filtered, washed the wet cake using a small amount of water and dried the wet cake under vacuum at room temperature for 4 hours to obtain fenofibrate Form IV (75 mg, 75% yield).

Example 11

Dispersed fenofibrate Form I (100 mg) in ethanol (5 mL) to form a suspension, filtered to obtain a saturated solution, added seed crystal of fenofibrate Form IV (1 mg) to the saturated solution, evaporated at room temperature to remove solvent (4 mL) to crystallize, filtered, washed the wet cake using a small amount of water and dried under vacuum at room temperature for 4 hours to obtain fenofibrate Form IV (72 mg, 72% yield). The yield was 72%.

Example 12

Dispersed fenofibrate Form I (100 mg) in ethanol (5 mL) to form a suspension, placed the suspension in a 50° C. water bath and stirred until dissolved, cooled to 40° C. to form a saturated solution, then slowly cooled to 10° C., filtered, washed the wet cake using a small amount of water, dried under vacuum for 4 hours at room temperature to obtain fenofibrate Form IV (51 mg, 51% yield).

XRPD patterns, DSC patterns and IR patterns (not shown) of the products obtained in Examples 2 to 12 were the same or similar as the product obtained in Example 1, indicating the Forms obtained in Examples 2 to 12 were the same as that in Example 1.

Comparative Example 1

Stability experiments, grinding tests and solubility experiments were performed on Form I and Form IV.

Stability experiments: Form IV of fenofibrate and the known Form I were evenly distributed in open petri dishes to form a thin layer with less than 5 mm in thickness, respectively. They were placed at 4500±500 lx light exposure, and 90±5% RH humidity chamber at 25° C., respectively. The XRPD results of the 5th day and 10th day were compared with that of the 0th day. The results shown in Table 1 indicated that neither Form I nor Form IV changed its corresponding pattern.

Grinding tests: placed 100 mg of Form IV of fenofibrate and the known Form I in a ball mill, respectively, grounded for 10 minutes at 20 Hz, compared its XRPD patterns with the unground samples. The results in Table 1 showed that neither Form I nor Form IV changed its corresponding pattern.

Solubility test at room temperature: placed 10 mg of Form IV of fenofibrate and 10 mg of the known Form I in two separate vials. Added 5 mL 0.5% Tween 80 aqueous solution and stirred at room temperature for 1 hours at 120 r/min, filtered, and the filtrates were analyzed by ultraviolet spectrophotometry. The solubility of Form IV and Form I was 0.079 g/L and 0.049 g/L, respectively, i.e., the solubility of Form IV was 1.6 times that of Form I. The result demonstrated that Form IV of the present invention has higher solubility.

TABLE 1

Stability experiments and grinding tests of Forms of fenofibrate. The results of stability experiments and grinding tests

| Starting form | Light exposure for 10 days | High humidity for 10 days | Grinding for 10 min |
|---|---|---|---|
| Form I | Form I | Form I | Form I |
| Form IV | Form IV | Form IV | Form IV |

The results indicate that Form IV of fenofibrate has good stability and its solubility is higher than that of the known Form I.

The described above are only specific embodiments for illustrating the present invention, but without limiting it thereto. Any changes or alternations, without creative work, made by those skilled in the art within the technical scope disclosed by the present invention, should fall within the scope of the present invention. Therefore, the scope of the present invention should be defined by the claims.

The invention claimed is:

1. Form IV of fenofibrate having the structure shown in formula (I) below,

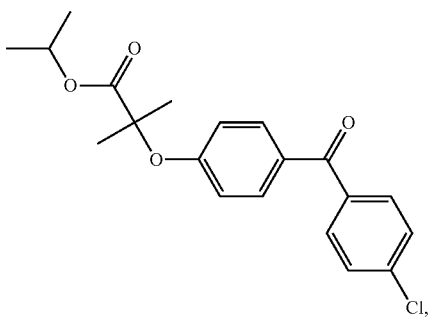 [SMILES: CC(C)OC(=O)C(C)(C)Oc1ccc(C(=O)c2ccc(Cl)cc2)cc1]

wherein the X-ray powder diffraction pattern of the Form IV of fenofibrate, expressed as 2θ angles, has the following characteristic peaks: 14.15±0.2°, 15.94±0.2°, 16.49±0.2°, 17.45±0.2°, 20.21±0.2°, and 22.87±0.2°.

2. The Form IV of fenofibrate according to claim 1, wherein the X-ray powder diffraction pattern of the Form IV of fenofibrate, expressed as 2θ angles, has the following characteristic peaks: 7.98±0.2°, 9.82±0.2°, 12.96±0.2°, 14.15±0.2°, 15.94±0.2°, 16.49±0.2°, 17.45±0.2°, 17.99±0.2°, 18.79±0.2°, 20.21±0.2°, 22.87±0.2°, and 26.17±0.2°.

3. The Form IV of fenofibrate according to claim 2, wherein the X-ray powder diffraction pattern of the Form IV of fenofibrate, expressed as 2θ angles, has the following characteristic peaks with their relative intensities:

| 2θ | Relative intensity % |
|---|---|
| 7.98 | 13.7 |
| 9.82 | 12.5 |
| 12.96 | 11.1 |
| 14.15 | 50.9 |
| 15.94 | 41.5 |
| 16.49 | 70.4 |
| 17.45 | 60.8 |
| 17.99 | 25.9 |
| 18.79 | 24.8 |
| 19.81 | 23.7 |
| 20.21 | 72.4 |
| 22.87 | 100 |
| 23.57 | 43.9 |
| 23.96 | 22.7 |
| 24.48 | 9.7 |
| 24.81 | 20.0 |
| 26.17 | 33.9 |
| 27.31 | 12.3 |
| 28.80 | 13.5 |
| 30.66 | 23.9 |
| 31.22 | 10.2. |

4. The Form IV of fenofibrate according to claim 1, wherein the Fourier transform infrared spectrum of the Form IV of fenofibrate, has characteristic peaks at wave numbers of 2985, 2936, 1737, 1650, 1596, 1499, 1468, 1389, 1314, 1258, 1149, and 1093 $cm^{-1}$.

5. A method of preparing the Form IV of fenofibrate according to claim 1, comprising the following steps: mixing Form I of fenofibrate and a polymer material, adding a solvent, stirring and mixing uniformly, heating until melting, cooling to crystallize, filtering, washing the filter cake, drying to obtain the Form IV of fenofibrate; wherein: the polymer material is 1% to 20% by weight of the fenofibrate; and the solvent is a protic solvent.

6. The method of claim 5, wherein the polymer material is polyvinylpyrrolidone or polyethylene glycol.

7. The method of claim 5, wherein the polymer material is 5% to 10% by weight of the fenofibrate.

8. The method of claim 5, wherein the solvent is water.

9. The method of claim 5, wherein the weight to volume ratio of the fenofibrate and the solvent is from 100 mg/mL to 1000 mg/mL.

10. The method of claim 9, wherein the weight to volume ratio of the fenofibrate and the solvent is from 100 mg/mL to 200 mg/mL.

11. The method of claim 5, wherein the melting temperature is from 80° C. to 100° C.

12. The method of claim 11, wherein the melting temperature is from 85° C. to 92° C.

13. The method of claim 5, wherein the cooling crystallization temperature is from −20° C. to 30° C.

14. The method of claim 13, wherein the cooling crystallization temperature is room temperature.

* * * * *